United States Patent
Fukuda (10) Patent No.: US 8,998,859 B2
(45) Date of Patent: Apr. 7, 2015

(54) MEDICAL NEEDLE AND PUNCTURING INSTRUMENT

(75) Inventor: Mitsuo Fukuda, Nishinomiya (JP)

(73) Assignee: Lightnix, Inc., Hyogo (JP)

( * ) Notice: Subject to any disclaimer, the term of this patent is extended or adjusted under 35 U.S.C. 154(b) by 169 days.

(21) Appl. No.: 13/582,353

(22) PCT Filed: Mar. 2, 2011

(86) PCT No.: PCT/JP2011/054744
§ 371 (c)(1),
(2), (4) Date: Aug. 31, 2012

(87) PCT Pub. No.: WO2011/111580
PCT Pub. Date: Sep. 15, 2011

(65) Prior Publication Data
US 2013/0006147 A1  Jan. 3, 2013

(30) Foreign Application Priority Data
Mar. 10, 2010 (JP) ................. 2010-053881

(51) Int. Cl.
*A61M 5/32* (2006.01)
*A61B 5/151* (2006.01)
*A61B 5/15* (2006.01)
*A61B 10/00* (2006.01)
*A61B 10/02* (2006.01)
*A61M 37/00* (2006.01)

(52) U.S. Cl.
CPC ........... *A61B 5/15142* (2013.01); *A61B 5/1411* (2013.01); *A61B 10/0045* (2013.01);
(Continued)

(58) Field of Classification Search
CPC ............... A61B 5/15; A61B 5/150007; A61B 5/150015; A61B 5/150022; A61B 5/15003; A61B 5/150038; A61B 5/150045; A61B 5/150053; A61B 5/150061; A61B 5/150068; A61B 5/150076; A61B 5/150083; A61B 5/150091; A61B 5/150099; A61B 5/150106; A61B 5/150114; A61B 5/150122; A61B 5/150129; A61B 5/1411; A61B 5/150458; A61B 5/150427; A61B 5/15045; A61B 5/01
USPC ............................. 600/4, 206, 435, 573, 604
See application file for complete search history.

(56) References Cited

U.S. PATENT DOCUMENTS 3,072,122 A    1/1963  Rosenthal
6,887,254 B1 *  5/2005  Curie ........................ 606/181
(Continued)

FOREIGN PATENT DOCUMENTS

EP    1759633 A1   3/2007
JP    2003116821 A  4/2003
(Continued)

OTHER PUBLICATIONS

International Search Report PCT/ISA/210 for International Application No. PCT/JP2011/054744 dated Mar. 23, 2011.
(Continued)

*Primary Examiner* — Max Hindenburg
*Assistant Examiner* — Renee Danega
(74) *Attorney, Agent, or Firm* — Harness, Dickey & Pierce, P.L.C.

(57) ABSTRACT

Provided are a medical needle and a puncturing instrument which make it possible to administer a predetermined amount of a substance to be administered into a living body and/or collect a predetermined amount of an object to be collected from within the living body with ease and accuracy. A medical needle (1) is provided with a puncturing part (10) which can penetrate into the living body. The puncturing part (10) has a pair of planar portions (12, 12) which are parallel to each other in an outer surface and a retaining chamber (18) defined within the puncturing part (10), the retaining chamber (18) passing through the puncturing part (10) and opening to the pair of planar portions (12) on each side. A puncturing instrument can be structured by accommodating the medical needle (1) in a casing in such a way that the medical needle (1) can project therefrom.

17 Claims, 8 Drawing Sheets

(52) U.S. Cl.
CPC ....... *A61B10/0233* (2013.01); *A61B 5/150022* (2013.01); *A61B 5/150282* (2013.01); *A61B 5/150419* (2013.01); *A61B 5/150427* (2013.01); *A61B 5/15045* (2013.01); *A61B 5/150916* (2013.01); *A61B 5/150969* (2013.01); *A61B 5/15105* (2013.01); *A61B 5/15113* (2013.01); *A61B 5/15117* (2013.01); *A61B 5/15144* (2013.01); *A61B 5/150458* (2013.01); *A61B 5/15186* (2013.01); *A61M 37/0015* (2013.01); *A61B 5/150259* (2013.01)

(56) References Cited

U.S. PATENT DOCUMENTS

| | | | |
|---|---|---|---|
| 8,142,366 | B2 | 3/2012 | Haar et al. |
| 2003/0028125 | A1 | 2/2003 | Yuzhakov et al. |
| 2004/0204750 | A1 | 10/2004 | Dinh |
| 2007/0078414 | A1* | 4/2007 | McAllister et al. ........... 604/272 |
| 2008/0103415 | A1* | 5/2008 | Roe et al. ...................... 600/583 |
| 2012/0089050 | A1 | 4/2012 | Fukuda |

FOREIGN PATENT DOCUMENTS

| | | |
|---|---|---|
| JP | 2004305753 A | 11/2004 |
| JP | 2008029710 A | 2/2008 |
| JP | 2009502447 A | 1/2009 |
| WO | WO-0207813 A1 | 1/2002 |
| WO | WO-2009148133 A1 | 12/2009 |

OTHER PUBLICATIONS

Supplementary European Search Report issued in corresponding European Patent Application No. 11753239, dated Jun. 13, 2013.

* cited by examiner

MEDICAL NEEDLE AND PUNCTURING INSTRUMENT

CROSS-REFERENCE TO RELATED APPLICATION(S)

This application is a National Stage of International Application No. PCT/JP2011/054744, filed Mar. 2, 2011, which claims priority to Japanese Patent Application No 2010-053881, filed on Mar. 10, 2010. The entire disclosures of each of the above applications are incorporated herein by reference.

TECHNICAL FIELD

The present invention relates to a medical needle for use in administering a drug or the like into a body and/or collecting blood, a body fluid or a tissue, for instance. The present invention further relates to a puncturing instrument provided with such a medical needle.

BACKGROUND ART

Figure 25:
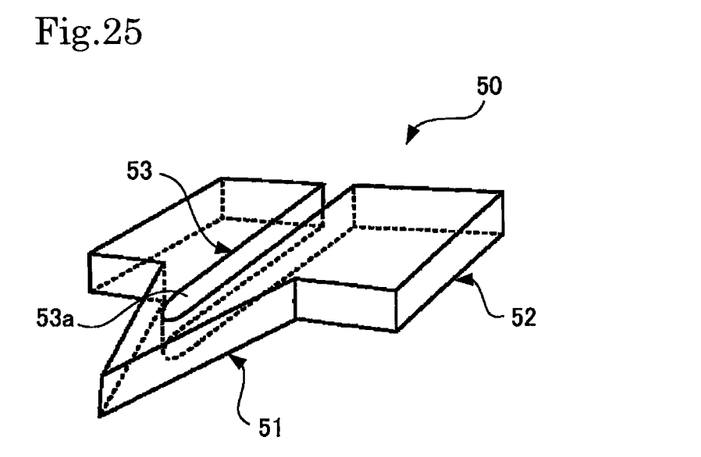
FIG. 25 is a perspective view of a conventional medical needle.

Medical needles, such as needles for injection and lancets, that have been developed in recent years include less invasive products which are unlikely to produce pain or an unpleasant feeling as disclosed in Patent Document 1, for example. As depicted in FIG. 25, a skin-piercing element 50 disclosed in Patent Document 1 is provided with a distal portion 51 and a proximal portion 52, the distal portion 51 being formed to have a sharp end that is penetrable into a living body. As a fluid pathway 53 runs from the distal portion 51 to the proximal portion 52, a physiological sample collected in an opening 53a in the distal portion 51 of the fluid pathway 53 is guided to the proximal portion 52 due to a capillary force.

PRIOR ART DOCUMENTS

Patent Document

Patent Document 1: Japanese Patent Application Publication No. 2003-116821

SUMMARY OF INVENTION

Technical Problem

According to the above-described configuration disclosed in Patent Document 1, the physiological sample collected by the distal portion 51 of the fluid pathway 53 flows toward the proximal portion 52. Thus, this configuration is not suited to an application in which a specified amount of physiological sample should be collected. Also, when it is intended to administer a drug into a body through the fluid pathway 53, it is difficult to precisely administer a prescribed quantity of the drug.

Under such circumstances, it is an object of the present invention to provide a medical needle which makes it possible to administer a predetermined amount of a substance to be administered into a living body and/or collect a predetermined amount of an object to be collected from within a living body with ease and accuracy.

It is another object of the present invention to provide a puncturing instrument provided with the aforementioned medical needle.

Solution to Problem

The aforementioned object of the present invention is accomplished by a medical needle including a puncturing part which can penetrate into a living body, the puncturing part having a pair of planar portions which are parallel to each other in an outer surface and a retaining chamber defined within the puncturing part, the retaining chamber passing through the puncturing part and opening to the pair of planar portions on each side.

In this medical needle, it is preferable that the retaining chamber be formed in a tapered shape so as to increase in diameter toward one or both of the pair of planar portions from inside the puncturing part.

A single retaining chamber or a plurality of retaining chambers may be formed in the puncturing part. In a case where a plurality of retaining chambers are formed, it is preferable to form the retaining chambers with a spacing provided between each retaining chamber along a puncturing direction of the puncturing part.

The aforementioned medical needle may be made of a biodegradable material so that an entirety of the medical needle can penetrate into the living body and be left therein. Optionally, the medical needle may be configured to further include a holding part for supporting the puncturing part from outside the living body.

The aforementioned object of the present invention is accomplished by a puncturing instrument including the aforementioned medical needle and a casing accommodating the medical needle in such a manner that the medical needle can project from the puncturing instrument.

Advantageous Effects of Invention

The present invention can provide a medical needle which makes it possible to administer a predetermined amount of a substance to be administered into a living body and/or collect a predetermined amount of an object to be collected from within a living body with ease and accuracy. The present invention can also provide a puncturing instrument including the aforementioned medical needle.

DESCRIPTION OF EMBODIMENTS

Figure 1:
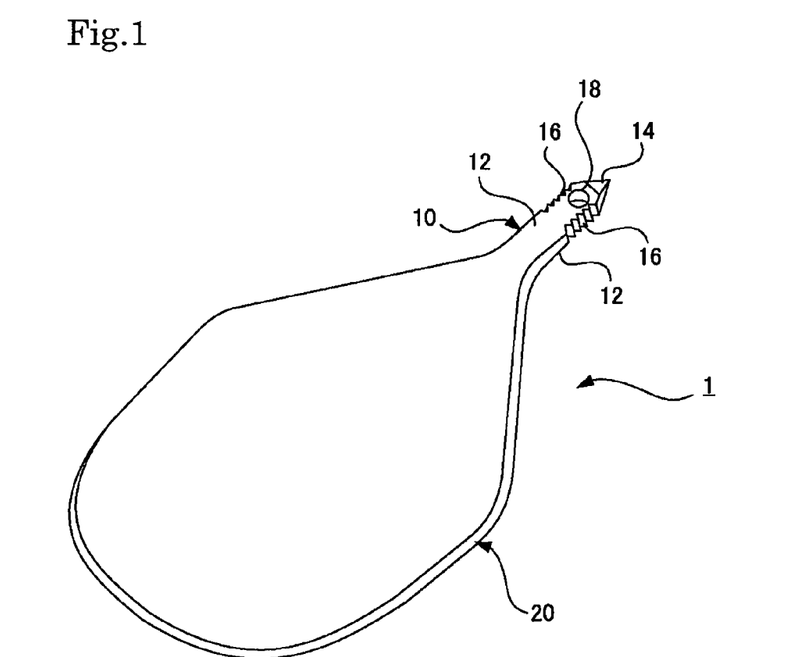
FIG. 1 is a perspective view of a medical needle according to an embodiment of the present invention.
Figure 2:
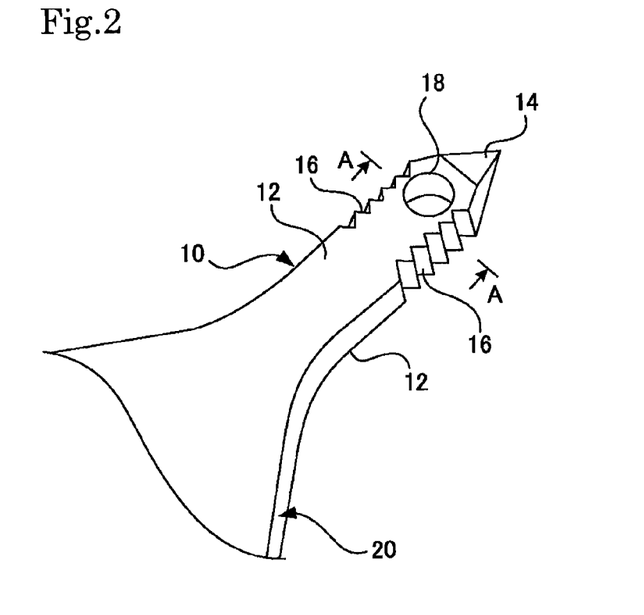
FIG. 2 is an enlarged view of a principal portion of FIG. 1.
Figure 3:
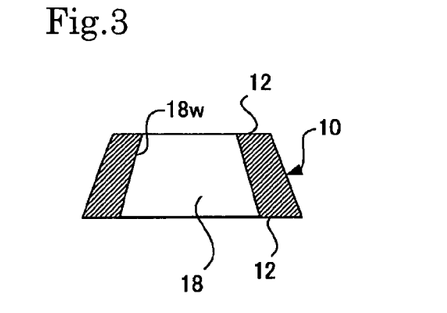
FIG. 3 is a cross-sectional view taken along line A-A of FIG. 2.

Descriptions of embodiments are described hereinbelow with reference to the accompanying drawings. FIG. 1 is a perspective view of a medical needle according to an embodiment of the present invention, FIG. 2 is an enlarged view of a principal portion of FIG. 1, and FIG. 3 is a cross-sectional view taken along line A-A of FIG. 2. In the discussion provided hereunder referring to the individual drawings, constituent elements having like functions are designated by the same symbols and a detailed description of such elements may be omitted.

As depicted in FIGS. 1 and 2, a medical needle 1 includes a puncturing part 10 having a forwardly narrowing shape and a holding part 20 formed to connect to a rear end of the puncturing part 10, the medical needle 1 having in an entirety thereof a platelike shape.

The puncturing part 10 has planar portions 12, 12 on front and back faces and a pointed tip 14 at an extreme end that can pierce the skin. What is essential herein is that the puncturing part 10 should have a pair of planar portions 12, 12 which are parallel to each other. While the puncturing part 10 of this embodiment has a trapezoidal shape when cut in cross section perpendicular to a puncturing direction, the puncturing part 10 of the present invention is not limited thereto. The cross section of the puncturing part 10 may have, other than the trapezoidal shape, any of such cross-sectional shapes as a rectangular or polygonal shape, or a shape formed by cutting a curved outer surface of a portion having a circular or elliptical cross section along an axial direction to form planar portions which are parallel to each other.

On both widthwise sides of the puncturing part 10, there are formed sawtooth-shaped corrugations 16, 16 to facilitate penetration of the puncturing part 10 into a living body. While the corrugations 16 are formed to have a length in the puncturing direction approximately equal to half the length of the puncturing part 10 as measured from the extreme end thereof in this embodiment, it is possible to determine the length of the corrugations 16 as appropriate so that the entirety of the puncturing part 10 can smoothly penetrate into the living body. Also, the corrugations 16 are not essential in this embodiment and the puncturing part 10 may be configured without the provision of the corrugations 16 provided that the puncturing part 10 can be pierced into the living body with the aid of the pointed tip 14. While the puncturing part 10 is configured to have approximately a constant width all the way from a base portion of the pointed tip 14 toward the rear along the puncturing direction in this embodiment, the puncturing part 10 may be configured to become gradually wider toward the rear. Optionally, the puncturing part 10 may be configured to become narrower (or such that the width becomes smaller) toward the rear. This configuration will be particularly suited for applications where it is desired to maintain the medical needle 1 in a state in which the puncturing part 10 is left penetrated into the living body. The object of the living body into which the puncturing part 10 may be pierced is any of such objects as a cell, a tissue, an internal organ, an alimentary canal, a blood vessel, a nerve, a skin, a muscle, an eyeball, and so forth.

In the puncturing part 10, there is formed a retaining chamber 18 made of a through hole which passes through the front and back faces of the puncturing part 10, both ends of the retaining chamber 18 opening to the pair of planar portions 12, 12. The retaining chamber 18 is located at a specified position from the extreme end of the puncturing part 10 (e.g., 300 to 800 μm from the extreme end) so that the retaining chamber 18 is defined within the puncturing part 10. The puncturing part 10 preferably has a length that allows the retaining chamber 18 to reach a desired depth in the living body, preferably about 0.2 to 300 mm, for example.

The retaining chamber 18 can be filled with an object to be collected, such as blood, a body fluid or a tissue when penetrated through the skin of the living body to collect this kind of object. Alternatively, the retaining chamber 18 may be filled in advance with a substance to be administered, such as a drug to be administered into the living body, and then penetrated into a specified part of the living body to administer the substance to be administered with pinpoint accuracy. While the medical needle 1 of this embodiment is capable of administering a substance to be administered into the living body and collecting an object to be collected from within the living body, the medical needle may be configured to perform only one of these functions. The substance to be administered and the object to be collected may be any of various types including a liquid, a solid, a semisolid (gel), a freeze-dried material and a nanoparticulate material.

Since the retaining chamber 18 is formed to open to both of the planar portions 12, 12 it is possible to precisely determine the volumetric capacity of the retaining chamber 18. Also, the retaining chamber 18 is defined within the puncturing part 10 which can be pierced into the living body without extending to the holding part 20 which is located outside the living body. Therefore, it is possible to accommodate and retain an exact predetermined amount of the substance to be administered or the object to be collected in the retaining chamber 18.

The puncturing part 10 can be pierced into and pulled out of the living body by grasping the holding part 20 which is always located outside the living body by hand or a tool. The puncturing part 10 may be pulled out instantly after piercing or after leaving the same within the living body for a while depending on the type of drug or a method of administration. This makes it possible to release a precise quantity of a drug into the living body or collect only a necessary amount of an object to be collected for measurement, for example. While the retaining chamber 18 is not particularly limited in size, the retaining chamber 18 typically has a volumetric capacity of 0.001 μl to 1 ml and an opening area of about 0.1 μm$^2$. Preferably, the retaining chamber 18 has an aspect ratio (length/diameter) set within a range of 0.1 to 5, for example.

The holding part 20 is formed to become remarkably wider from the rear end of the puncturing part 10 so that the holding part 20 does not intrude into the living body and the holding part 20 can support the puncturing part 10 from outside the living body. The holding part 20 is not particularly limited in shape or size.

The puncturing part 10 may be made of a biocompatible material. Biocompatible materials include macromolecular polymers, biopolymers, proteins and biocompatible inorganic materials, for example.

Macromolecular polymers that may preferably be used are those usable for medical applications. Examples of such polymers include polyvinyl chloride, polyethylene glycol, parylene, polyethylene, polypropylene, silicone, polyisoprene, polymethyl methacrylate, fluororesins, polyether imide, polyethylene oxide, polyethylene terephthalate, polyethylene succinate, polybutylene terephthalate, polybutylene succinate, polybutylene succinate/carbonate, polyphenylene oxide, polyphenylene sulfide, polyformaldehyde, polyanhydride, polyamide (nylon 6, nylon 66), polybutadiene, polyvinyl acetate, polyvinyl alcohol, polyvinyl-pyrrolidone, polyesteramide, polymethyl methacrylate, polyacrylonitrile, polysulfone, polyether sulfone, acrylonitrile-butadiene-styrene (ABS) resins, polycarbonate, polyurethanes (polyetherurethane, polyesterurethane, polyetherurethaneurea), polyvinylidene chloride, polystyrene, polyacetal, polybutadiene, ethylene-vinyl acetate copolymers, ethylene-vinyl alcohol copolymers, ethylene-propylene copolymers, polyhydroxyethyl methacrylate, polyhydrobutyrate, polyorthoester, polylactic acid, polyglycol, polycaprolactone, polylactic acid copolymers, polyglycolic acid-glycol copolymers, polycapronolactone copolymers, polydioxanone, perfluoroethylene-propylene copolymers, cyanoacrylate polymers, polybutyl cyanoacrylate, polyaryl ether ketone, epoxy resins, polyester resins, polyimide, phenolic resins, acrylic resins, and the like.

Examples of the biopolymers include cellulose, starch, chitin and chitosan, agar, carrageenan, alginic acid, agarose, pullulan, mannan, curdlan, xanthane gum, gellan gum, pectin, xyloglucan, guar gum, lignin, oligosaccharide, hyaluronic acid, schizophyllan, lentinan, and the like. Examples of the proteins include collagen, gelatin, keratin, fibroin, glue, sericin, vegetable proteins, milk proteins, egg proteins, synthetic proteins, heparin, nucleic acid and the like, as well as sugar, candies, glucose, malt sugar, sucrose, maltose, simple sugars, polysaccharides and polymer alloys thereof.

Examples of the biocompatible inorganic materials include ceramics such as glass, nanocomposite ceramics, $Al_2O_3/ZrO_2$ composite ceramics, $Si_3N_4$ nanocomposite materials, hydroxyapatite, calcium carbonate, carbon, graphite (nanografibers), carbon nanotube (CNT), fullerene composite materials, hydroxyapatite polymer composite materials, cobalt-chromium alloys, stainless steel, titanium, titanium alloys, and the like.

Among these biocompatible materials, it is preferable to use a biodegradable material selected from biodegradable polymers including, for example, polylactic acid, polyglycolic acid, polycaprolactone, collagen, starch, hyaluronic acid, alginic acid, chitin, chitosan, cellulose or gelatin as well as compounds thereof. This is because such materials decompose in the presence of microorganisms and thus can easily be discarded after use.

It is particularly preferable to use a material selected from polylactic acid, polyglycolic acid, polycaprolactone, polydioxanone and copolymers thereof. This is because such materials have a proper level of affinity with such body composition fluids as blood and body fluids and, therefore, this kind of material makes it easy to accommodate the body composition fluid in the retaining chamber 18 and prevent excessive adsorption of components contained in the body composition fluid.

In case where the puncturing part 10 is made of such a biocompatible material, it is preferable that the entirety of outer surfaces of the puncturing part 10 be processed for improving biocompatibility. It is particularly preferable to perform such processing to improve the biocompatibility thereof on an inside wall surface of the retaining chamber 18. The processing for the biocompatibility improvement is a surface treatment applied to modify a surface that goes into contact with the body composition fluid or to coat a surface treatment agent on the surface for adjusting the affinity with the body composition fluid for making it easier to control adsorption of components contained in the body composition fluid.

The biocompatibility improvement processing for adjusting the affinity with the body composition fluid can be performed by coating and fixing such a medium as polyethylene glycol, sodium hydroxide, citric acid, polyoxyethylene polyoxypropylene glycol, polysorbate, Poloxamer, silicone, or the like.

Also, the biocompatibility improvement processing for making it easier to control adsorption of components contained in the body composition fluid can be performed by coating and fixing such a medium as heparin, phosphoric acid, polyethylene glycol, sodium hydroxide, citric acid, polyoxyethylene polyoxypropylene glycol, polysorbate, Poloxamer, silicone, or the like.

Although not particularly restricted, it is possible to evaluate the affinity with the body composition fluid by the angle of contact, and if a properly chosen level of affinity is achieved by using this approach, it is possible to make it easier to accommodate the body composition fluid within the retaining chamber 18. On the other hand, it is preferable that adsorption of components of the body composition fluid be avoided as much as possible within a range in which the affinity with the body composition fluid is not jeopardized.

Although it is possible to fabricate the holding part 20 with a material differing from the material of the puncturing part 10, it is preferable to fabricate the holding part 20 integrally with the puncturing part 10 using the same material. As an example, it is possible to fabricate the puncturing part 10 and the holding part 20 as a one-piece component using any of the aforementioned materials by means of a molding unit including upper and lower dies.

The retaining chamber 18 in the puncturing part 10 is preferably structured during a process of injection molding with a projecting part corresponding to the retaining chamber 18 formed in one or both of the upper and lower dies so that the location and volumetric capacity of the retaining chamber 18 are precisely determined. This kind of molding method is particularly effective when the volumetric capacity of the retaining chamber 18 is extremely small (e.g., 100 nanoliters or less). Depending on the size of the retaining chamber 18, however, it is possible to form the retaining chamber 18 by microfabrication laser machining using an excimer laser or a femtosecond laser or by cutting tool machining, for example.

Although it is possible to form the retaining chamber 18 in a straight cylindrical shape, the retaining chamber 18 is formed in a tapered shape in this embodiment so that the retaining chamber 18 becomes larger in diameter from the planar portion 12 on the front face side toward the planar portion 12 on the back face side as depicted in the cross-sectional view of FIG. 3. Compared to a case where the retaining chamber 18 is formed in a straight cylindrical shape, such a shape of the retaining chamber 18 makes it possible to increase an actual contact area between an inside wall surface 18w of the retaining chamber 18 and the substance to be administered or the object to be collected, easily retain the substance to be administered or the object to be collected within the retaining chamber 18, and easily administer the substance to be administered or collect the object to be collected through an enlarged opening. Effects resulting from an increase in the contact area are particularly significant when the retaining chamber 18 is extremely small (e.g., 200 μm or less in opening diameter and 100 nanoliters or less in volumetric capacity). These effects can be produced by tapering the retaining chamber 18 so that the inside wall surface 18w thereof is inclined even at a slight angle with respect to a direction perpendicular to the planar portions 12.

Figure 4:
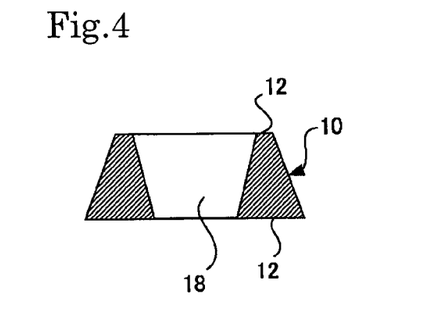
FIG. 4 is a cross-sectional view of a principal portion depicting a variation of the present invention.

While the retaining chamber 18 depicted in FIG. 3 is formed such that the diameter of the retaining chamber 18 increases from one of the planar portions 12 having a smaller area toward the other of the planar portions 12 having a larger area in the puncturing part 10 that has a trapezoidal shape in cross section to maintain volumetric capacity, the retaining chamber 18 may be formed in such a tapered shape that the diameter of the retaining chamber 18 increases from the planar portion 12 having a larger area toward the planar portion 12 having a smaller area as depicted in FIG. 4.

Figure 5:
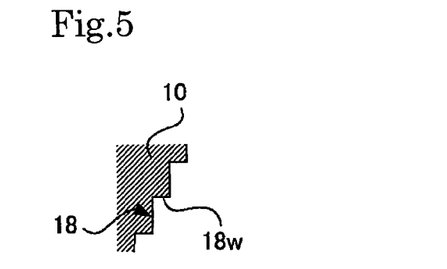
FIG. 5 is an enlarged cross-sectional view of a principal portion depicting another variation of the present invention.

Preferably, the inside wall surface of the retaining chamber 18 is a rough surface so as to further increase the contact area with the substance to be administered or with the object to be collected. For example, it is effective to form the inside wall surface 18w of the retaining chamber 18 in a steplike shape when viewed microscopically, as depicted in an enlarged view of FIG. 5.

Figure 6:
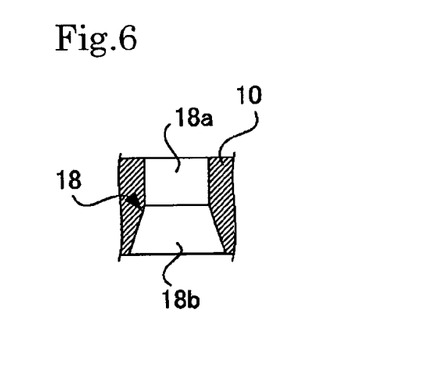
FIG. 6 is a cross-sectional view depicting still another variation of the present invention.

Instead of structuring the retaining chamber 18 in the trapezoidal shape so that the diameter of the retaining chamber 18 increases all the way along a thickness direction of the puncturing part 10 as depicted in FIG. 3, the retaining chamber 18 may be configured with a combination of a straight cylindrical portion 18a and a widening portion 18b as depicted in FIG. 6. Also, while the retaining chamber 18 is tapered so that the diameter thereof increases from inside the puncturing part 10 toward one of the planar portions 12 as depicted in FIGS. 3 and 6, the retaining chamber 18 may be configured with a pair of truncated cone-shaped widening portions 18c, 18d of which truncated ends are joined together so that the diameter of the retaining chamber 18 increases from inside the puncturing part 10 toward both of the planar portions 12, 12 as illustrated in FIG. 7.

Figure 7:
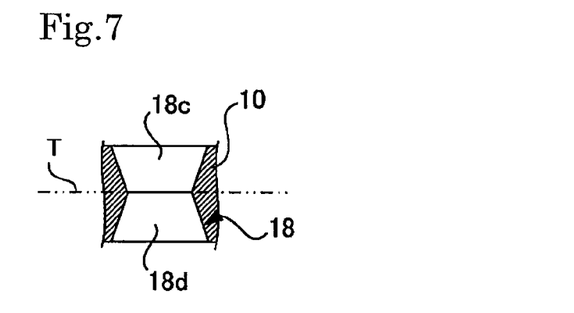
FIG. 7 is a cross-sectional view depicting still another variation of the present invention.
Figure 8:
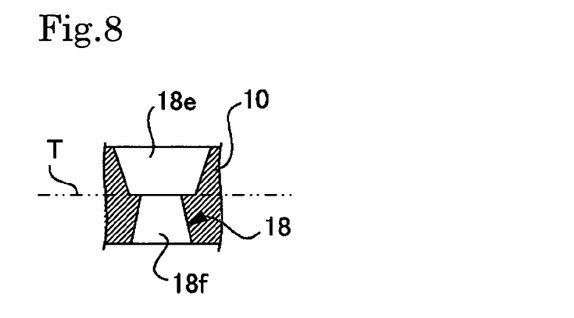
FIG. 8 is a cross-sectional view depicting still another variation of the present invention.

It is possible to structure the retaining chamber 18 depicted in FIG. 7 in a manner that a boundary between the two widening portions 18c, 18d is formed at a joint surface T between the upper and lower dies during the process of injection molding. In this case, if the area of a truncated end of one widening portion 18e is made larger than the area of a truncated end of the other widening portion 18f as depicted in FIG. 8, it is possible to obtain a shape in which the two truncated ends are reliably joined together even when a certain amount of misalignment occurs between the two widening portions 18e, 18f. This makes it possible to lessen the accuracy required for aligning the upper and lower dies at the joint surface T and facilitate molding operation.

Figure 9:
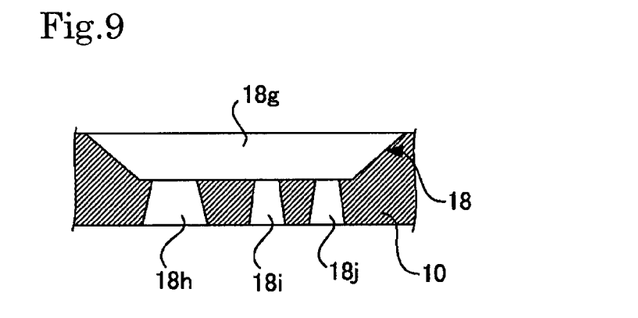
FIG. 9 is a cross-sectional view depicting still another variation of the present invention.

It is also possible to structure the retaining chamber 18 to include a plurality of widening portions 18g, 18h, 18i, 18j with truncated ends of a plurality of widening portions 18h, 18i, 18j joined to a truncated end of one widening portion 18g as depicted in FIG. 9. In this case, one or more of the widening portions 18g, 18h, 18i, 18j may be formed to have a straight cylindrical shape.

Figure 10:
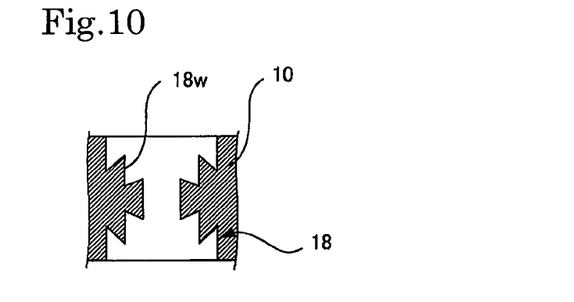
FIG. 10 is a cross-sectional view depicting still another variation of the present invention.
Figure 11:
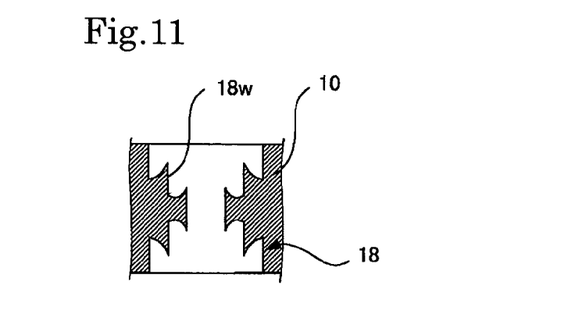
FIG. 11 is a cross-sectional view depicting still another variation of the present invention.

Furthermore, it is possible to structure the inside wall surface 18w of the retaining chamber 18 in a steplike fashion as a whole as depicted in FIG. 10. Although the inside wall surface 18w may be formed at right angles or at acute angles from one step to another as depicted in FIG. 10, it is possible to increase the contact area between the inside wall surface 18w and the substance to be administered or the object to be collected by shaping part (or all) of the inside wall surface 18w having originally straight line sections in cross-sectional view to have a curved profile as depicted in FIG. 11. This serves to enhance the ability of the retaining chamber 18 to retain the substance to be administered or the object to be collected. It is not necessarily to form steps in the retaining chamber 18 that are depicted in FIGS. 10 and 11 all across the inside wall surface 18w of the retaining chamber 18 but such steps may be formed only in part of the inside wall surface 18w. Alternatively, steps formed in a particular part of the inside wall surface 18w may have a shape differing from that of steps formed in another part of the inside wall surface 18w.

Figure 12:
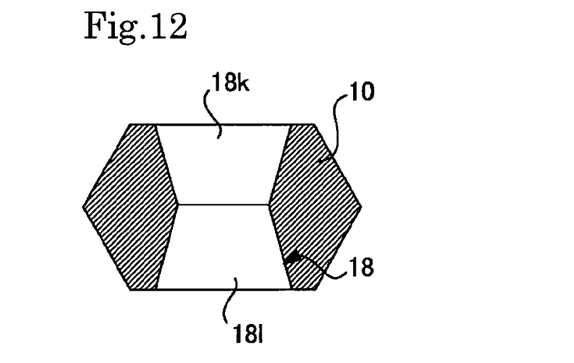
FIG. 12 is a cross-sectional view depicting still another variation of the present invention.
Figure 13:
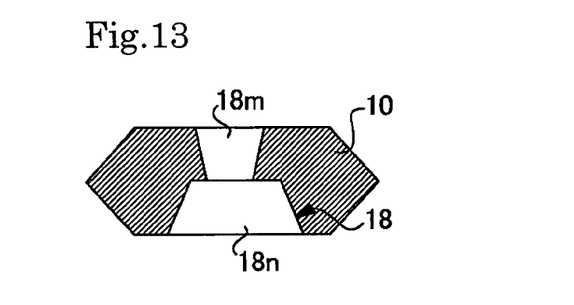
FIG. 13 is a cross-sectional view depicting still another variation of the present invention.

The retaining chamber 18 having a shape configured with a combination of a plurality of widening portions is also applicable to cases where the puncturing part 10 has a cross-sectional shape other than the trapezoidal shape. If the cross-sectional shape of the puncturing part 10 is hexagonal, for example, it is possible to employ a combination of two widening portions 18k, 18l whose truncated ends have the same area as depicted in FIG. 12 or a combination of two widening portions 18m, 18n whose truncated ends have different areas as depicted in FIG. 13.

Figure 14:
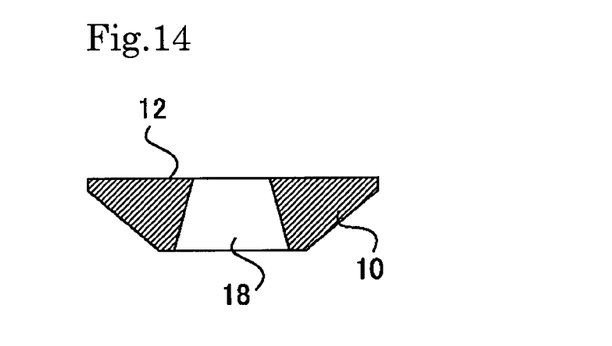
FIG. 14 is a cross-sectional view depicting still another variation of the present invention.

The hexagonal cross-sectional shape of the puncturing part 10 includes a case where the puncturing part 10 has a generally trapezoidal shape as depicted in FIG. 14. These puncturing parts 10 having a hexagonal cross section make it possible to reduce a cross-sectional area while maintaining mechanical strength and yet facilitating puncturing operation. Although the retaining chamber 18 of the puncturing part 10 depicted in FIG. 14 is formed with a single widening portion, it is possible to form the retaining chamber 18 with a plurality of widening portions in this configuration as well.

Figure 15:
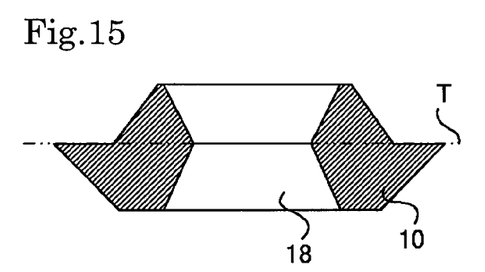
FIG. 15 is a cross-sectional view depicting still another variation of the present invention.
Figure 16:
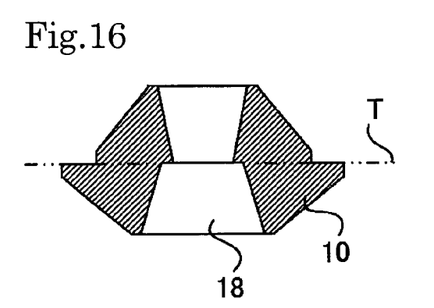
FIG. 16 is a cross-sectional view depicting still another variation of the present invention.
Figure 17:
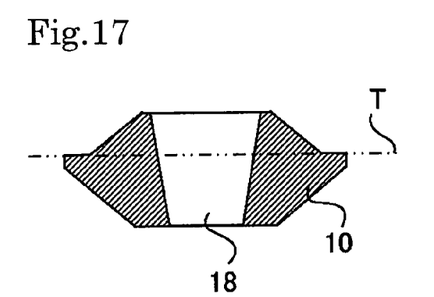
FIG. 17 is a cross-sectional view depicting still another variation of the present invention.

Also, in a case where the puncturing part 10 is fabricated by injection molding, portions formed by the upper and lower dies may differ in cross-sectional shape and/or size. Specifically, the puncturing part 10 may have a cross-sectional shape obtained by combining two trapezoidal shapes having different joint lengths (joint surface areas) at the joint surface T as depicted in FIG. 15, a cross-sectional shape obtained by combining two hexagonal shapes having different joint lengths at the joint surface T as depicted in FIG. 16, or a cross-sectional shape obtained by combining a trapezoidal shape and a hexagonal shape having different joint lengths at the joint surface T as depicted in FIG. 17. According to these configurations, it is possible to lessen the accuracy required for aligning the upper and lower dies at the joint surface T and facilitate molding operation. Additionally, it is possible to easily obtain a complex cross-sectional shape which enhance the mechanical strength of the puncturing part 10 and achieve a reduction in resistance to punctuation due to the reduced cross-sectional area while maintaining the volumetric capacity of the retaining chamber 18.

Figure 18:
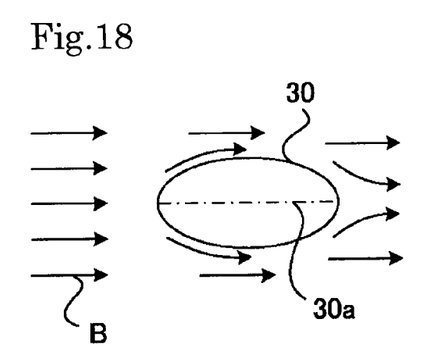
FIG. 18 is a schematic view for explaining an example of a molding method of the medical needle of the present invention.

Furthermore, while openings of the retaining chamber 18 have a circular shape in the present embodiment, the openings may be formed into various shapes including an elliptical shape, a rectangular shape and a polygonal shape. For example, when the medical needle 1 is fabricated by injection molding, it is preferable to form the projecting part of the molding unit to have an elliptical cross section so that the openings of the retaining chamber 18 have the elliptical shape, and determine a major axis 30a of the projecting part 30 so that the major axis 30a becomes parallel to an injecting direction (direction B) of material during the process of injection molding as illustrated in FIG. 18. According to such a method of forming the retaining chamber 18, it is possible to ensure a smooth flow of molding material around the projecting part 30 and maintain the accuracy of the volumetric capacity even if the retaining chamber 18 is extremely small.

Figure 19:
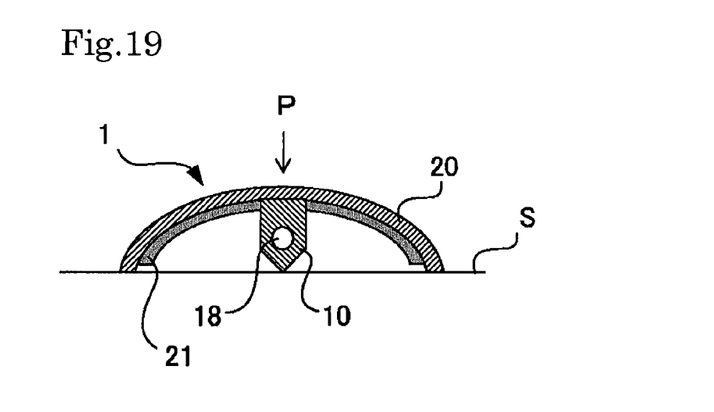
FIG. 19 is a cross-sectional view depicting still another variation of the present invention.
Figure 20:
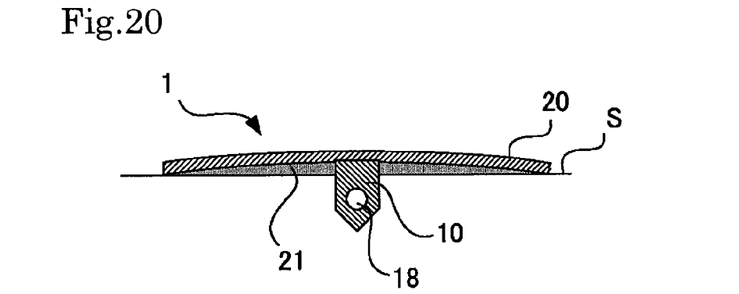
FIG. 20 is a cross-sectional view for explaining a method of use of a medical needle depicted in FIG. 19.

Furthermore, the medical needle of this embodiment may be configured such that the holding part 20 is formed into a suckerlike shape and the puncturing part 10 is erected from a middle part of an inside surface of the holding part 20 as depicted in FIG. 19. According to this configuration, if the middle part of the holding part 20 is forced in the direction of an arrow P during puncturing operation, the puncturing part 10 intrudes into the living body as depicted in FIG. 20, with the inside surface of the holding part 20 held in tight contact with a surface S of the living body due to elastic deformation of the holding part 20. In this configuration, it is preferable to provide an adhesive layer 21 made of an adhesive tape or the like on the inside surface of the holding part 20. This makes it possible to enhance adhesion between the holding part 20 and the surface S of the living body and maintain the puncturing part 10 in a desirable puncturing state for an extended period of time. The holding part 20 may be so machined as to form slits radially outward from the middle part to facilitate deformation and enhance adhesion to the surface S of the living body. Furthermore, the medical needle may be configured such that a plurality of puncturing parts 10 are formed on the inside surface of the suckerlike holding part 20.

Figure 21:
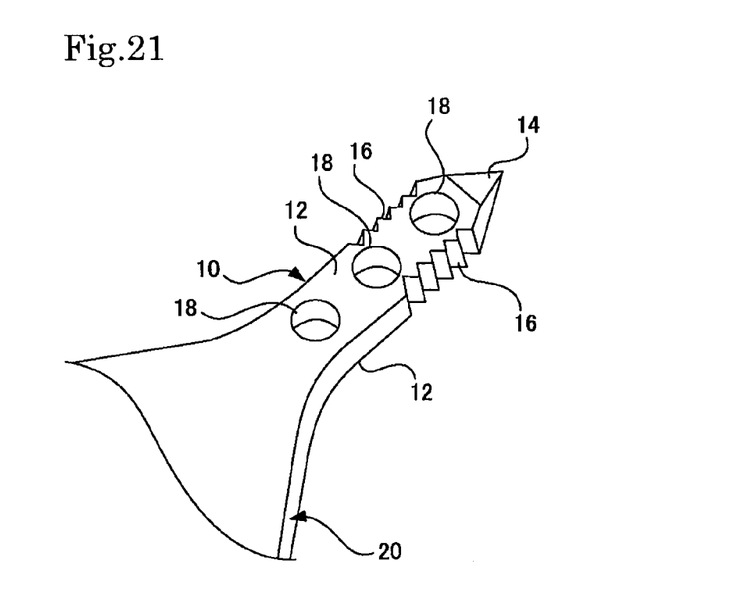
FIG. 21 is a perspective view depicting still another variation of the present invention.

The above-described individual embodiments employ a configuration in which one only retaining chamber 18 is formed in the puncturing part 10. According to this configuration, it is possible to precisely control the depth reached by a drug when the puncturing part 10 carrying the drug filled in the retaining chamber 18 pierces the living body. This configuration is therefore useful for vaccination, for instance. On the other hand, it is possible to form a plurality of retaining chambers 18 in the puncturing part 10 as depicted in FIG. 21. Preferably, the individual retaining chambers 18 are defined within the puncturing part 10 with a spacing formed between each retaining chamber 18 along the puncturing direction of the puncturing part 10. While the individual retaining chambers 18 are linearly arranged along the puncturing direction in the configuration depicted in FIG. 21, the retaining chambers 18 may be arranged at laterally offset positions. Also, the individual retaining chambers 18 may differ in shape, opening area and/or volumetric capacity, for example. Furthermore, the above-described various variations of the retaining chamber 18 are applicable to these retaining chambers 18.

Due to the puncturing part 10 having a constant puncturing depth, the puncturing part 10 depicted in FIG. 21 makes it possible to administer the substances to be administered or collect the objects to be collected at different parts of the living body along the direction of depth including an endodermic part, a hypodermic part and an intramuscular part, for example. When the plurality of retaining chambers 18 are used to administer substances to be administered, the substances may differ from one retaining chamber 18 to another. Alternatively, it is possible to administer the substance to be administered with one retaining chamber 18 while collecting the object to be collected with another retaining chamber 18 at the same time.

It is possible to use the medical needle of the present invention singly. Alternatively, it is also possible to use the medical needle of the present invention in a puncturing instrument in which the medical needle is projectably accommodated in a casing. Examples of such puncturing instruments include an indwelling needle system having the medical needle of any of the above-described embodiments as an inner needle element disposed inside a casing (an outer needle element) made of a soft material, as well as a puncture needle cartridge detachably mounted on a puncture device body and a puncture device which is singly usable for performing puncturing operation without requiring the puncture device body as disclosed in International Publication No. WO2009/148133 (pamphlet).

Figure 22:
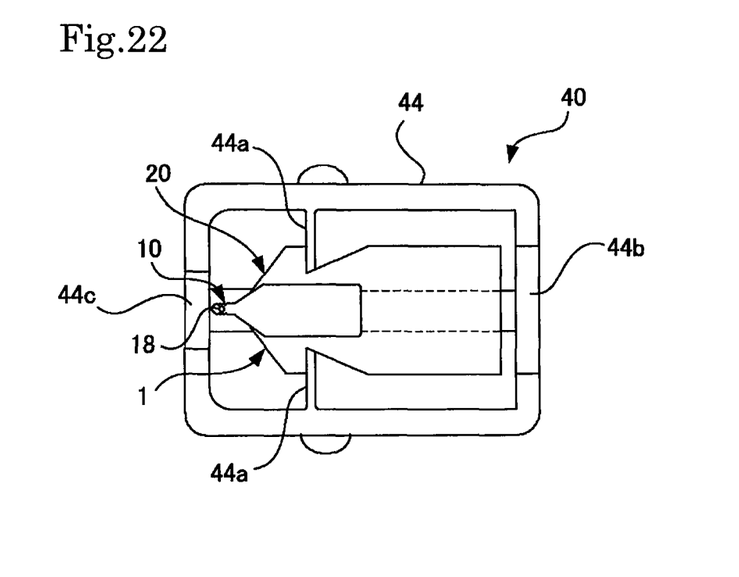
FIG. 22 is a plan view depicting a puncturing instrument according to an embodiment of the present invention.

A puncture needle cartridge 40 disclosed in International Publication No. WO2009/148133 (pamphlet) includes a medical needle 1 and a framelike casing 44 which accommodates the medical needle 1 as depicted in FIG. 22. The medical needle 1 includes a puncturing part 10 and a holding part 20, and a retaining chamber 18 is formed in the puncturing part 10. Provided on an inside wall surface of the casing 44 are a pair of flexible pieces 44a, 44a which are located at mutually opposed positions and meshed with the holding part 20. FIG. 22 depicts the casing 44 in a state in which an upper lid thereof is removed.

If a rear end of the medical needle 1 of this puncture needle cartridge 40 is pushed by a projecting member or the like through a rear opening 44b of the casing 44, the puncturing part 10 protrudes from a front opening 44c of the casing 44, making it possible to perform the puncturing operation. After performing the puncturing operation, the puncturing part 10 moves backward by the action of the flexible pieces 44a, 44a and are housed in the casing 44. Such a configuration of the puncturing instrument in which the medical needle is made movable forward and backward is particularly effective in cases where it is desired to quickly perform the puncturing operation at a desired depth (e.g., an endodermic part), such as vaccination against influenza. Incidentally, the puncturing instrument 40 is not limited to the configuration in which the medical needle 1 is made movable forward and backward within the casing 44 but may be so configured that the medical needle projects from the casing and held at a puncturing position (which means that the medical needle does not retract into the casing after projecting therefrom).

Figure 23:
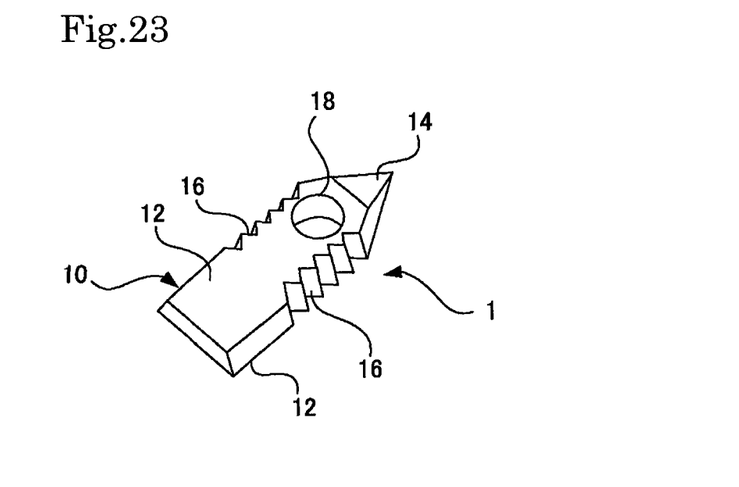
FIG. 23 is a perspective view depicting yet another variation of the present invention.

While the medical needles of the foregoing individual embodiments are configured to include the puncturing part 10 and the holding part 20 which supports the puncturing part 10 from outside the living body, it is possible to configure a medical needle 1 only comprising a puncturing part 10 without the holding part 20 as depicted in FIG. 23. As this medical needle 1 intrudes into the living body in an entirety thereof, it is preferable to form the medical needle 1 with a biodegradable material. By piercing the living body with this medical needle 1 with a retaining chamber 18 filled with the substance to be administered and leaving the puncturing part 10 in the living body, it is possible to cause the medical needle 1 to decompose within the living body and accelerate absorption of the administered substance. If the medical needle 1 is configured such that the entirety of the medical needle 1 can be penetrated into the living body and left therein, it becomes unnecessary to retrieve the needle. This makes it possible to solve a medical waste problem and is particularly effective in a drug delivery system (DDS). It goes without saying that the various variations of the retaining chamber 18 described earlier with reference to the medical needle 1 provided with the holding part 20 are also applicable to the medical needle 1 without the holding part 20 of this embodiment.

Figure 24:
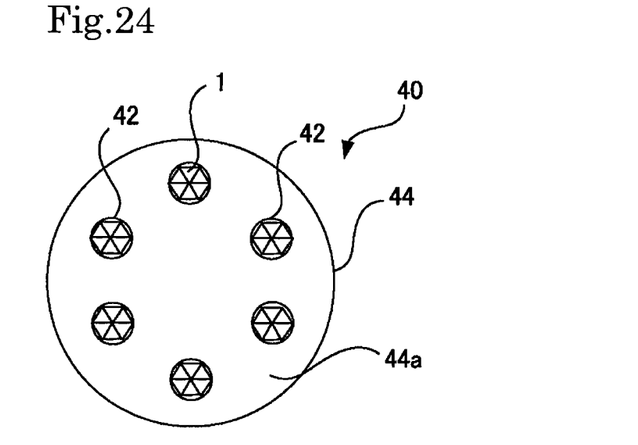
FIG. 24 is a front view depicting a puncturing instrument according to another embodiment of the present invention.

Medical needles 1 each comprising only the puncturing part 10 may be combined with a cylindrical casing 44 having a plurality of mounting sites 42 made of through holes to structure a puncturing instrument 40 as depicted in a front view of FIG. 24, for example. This puncturing instrument 40 is configured such that, under conditions where the medical needles 1 each comprising only the puncturing part are housed in the individual mounting sites 42 and a forward face 44a of the casing 44 is pressed against the surface of the living body, rear ends of the medical needles 1 are pushed forward by pushing means like plungers or compressed air so as to eject and penetrate the medical needles 1 into the living body. It is possible to control the depth of penetration of each medical needle 1 into the living body by regulating a pushing force exerted on each medical needle 1. The medical needles 1 may be pushed as a single entity by the same pushing force or pushed individually to achieve different depths of penetration.

The casing 44 may be provided with one mounting site 42 only. It is also possible to configure the casing 44 with an endoscope, for example. In this configuration, the medical needle 1 comprising only the puncturing part may be mounted in an extreme end of the endoscope, so that the medical needle 1 can be ejected by use of a guide wire or air pressure to puncture a desired part of the living body.

Since the medical needle and the puncturing instrument of the present invention can precisely administer the substance to be administered and collect the object to be collected even if the amount of the substance or the object is extremely small, the medical needle and the puncturing instrument have various applications including a drug delivery system (DDS) and a medical device for collecting and analyzing a minor component or a single cell, for example.

REFERENCE SIGNS LIST

1 Medical needle
10 Puncturing part
12 Planar portion
18 Retaining chamber
20 Holding part
40 Puncturing instrument
44 Casing

The invention claimed is:

1. A medical needle comprising:
a puncturing part to penetrate into a living body, the puncturing part having a pair of planar portions which are parallel to each other in an outer surface and a retaining chamber defined within the puncturing part, the retaining chamber passing through the puncturing part and opening to the pair of planar portions on each side; wherein
the retaining chamber has a tapered shape obtained by joining together truncated ends of at least two truncated cone-shaped widening portions such that the retaining chamber increases in diameter toward each of the pair of planar portions from inside the puncturing part.

2. The medical needle according to claim 1, wherein the puncturing part includes a plurality of retaining chambers spaced apart along a puncturing direction of the puncturing part.

3. The medical needle according to claim 1, wherein the medical needle is made of a biodegradable material so that an entirety of the medical needle can penetrate into the living body and be left therein.

4. The medical needle according to claim 1, further comprising:
a holding part configured to support the puncturing part from outside the living body.

5. A puncturing instrument comprising:
the medical needle according to claim 1; and
a casing configured to accommodate the medical needle such that the medical needle can project from the puncturing instrument.

6. The puncturing instrument according to claim 5, wherein the puncturing part includes a plurality of retaining chambers spaced apart along a puncturing direction of the puncturing part.

7. The puncturing instrument according to claim 5, wherein the medical needle is made of a biodegradable material so that an entirety of the medical needle can penetrate into the living body and be left therein.

8. The puncturing instrument according to claim 5, further comprising:
a holding part configured to support the puncturing part from outside the living body.

9. The puncturing instrument according to claim 5, wherein an area of a truncated end of a first of the at least two truncated cone-shaped widening portions is larger than an area of a truncated end of a second of the at least two truncated cone-shaped widening portions.

10. The puncturing instrument according to claim 5, wherein the at least two truncated cone-shaped widening portions include a plurality of first truncated cone-shaped widening portions having truncated ends joined to a truncated end of a second of the at least two truncated cone-shaped widening portions.

11. The medical needle according to claim 1, wherein an area of a truncated end of a first of the at least two truncated cone-shaped widening portions is larger than an area of a truncated end of a second of the at least two truncated cone-shaped widening portions.

12. The medical needle according to claim 1, wherein the at least two truncated cone-shaped widening portions include a plurality of first truncated cone-shaped widening portions having truncated ends joined to a truncated end of a second of the at least two truncated cone-shaped widening portions.

13. A medical needle comprising
a puncturing part configured to penetrate into a living body, the puncturing part having at least two planar portions and a retaining chamber, the retaining chamber being defined within the puncturing part, the retaining chamber passing through the puncturing part to provide an opening at outer surfaces of each of the at least two planar portions, the outer surfaces of the at least two planar portions being parallel to each other;
wherein the retaining chamber has at least two truncated cone-shaped widening portions, the at least two truncated cone-shaped widening portions being joined together such that a diameter of each of the at least two truncated cone-shaped widening portions increases from inside the puncturing part toward a respective one of the at least two planar portions; and
wherein the retaining chamber is configured to hold a substance to be administered to the living body.

14. The puncturing instrument according to claim 13, wherein an area of a truncated end of a first of the at least two truncated cone-shaped widening portions is larger than an area of a truncated end of a second of the at least two truncated cone-shaped widening portions.

15. The puncturing instrument according to claim 13, wherein the at least two truncated cone-shaped widening portions include a plurality of first truncated cone-shaped widening portions having truncated ends joined to a truncated end of a second of the at least two truncated cone-shaped widening portions.

16. The medical needle according to claim 13, wherein the retaining chamber is configured to release the substance into the living body when the puncturing part is inserted into the living body.

17. A medical needle comprising:
- a puncturing part configured to penetrate into a living body, the puncturing part having at least two planar portions and a retaining chamber, the retaining chamber being defined within the puncturing part, the retaining chamber passing through the puncturing part to provide an opening at outer surfaces of each of the at least two planar portions, the outer surfaces of the at least two planar portions being parallel to each other;
- wherein the retaining chamber has at least two truncated cone-shaped widening portions, the at least two truncated cone-shaped widening portions being joined together such that a diameter of each of the at least two truncated cone-shaped widening portions increases from inside the puncturing part toward a respective one of the at least two planar portions; and
- wherein the retaining chamber is configured to collect an object from within the living body when the puncturing part is inserted into the living body.

* * * * *